(12) United States Patent
Abreu

(10) Patent No.: US 12,178,742 B2
(45) Date of Patent: *Dec. 31, 2024

(54) THERAPEUTIC BED OR GURNEY FOR THERMAL DIAGNOSIS AND TREATMENT OF A HUMAN

(71) Applicant: Brain Tunnelgenix Technologies Corp., Aventura, FL (US)

(72) Inventor: Marcio Marc Abreu, Aventura, FL (US)

(73) Assignee: Brain Tunnelgenix Technologies Corp., Aventura, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/341,680

(22) Filed: Jun. 26, 2023

(65) Prior Publication Data

US 2023/0338186 A1    Oct. 26, 2023

Related U.S. Application Data

(63) Continuation of application No. 15/332,738, filed on Oct. 24, 2016, now Pat. No. 11,723,794.

(Continued)

(51) Int. Cl.
*A61F 7/02* (2006.01)
*A61F 7/00* (2006.01)
(Continued)

(52) U.S. Cl.
CPC ............... *A61F 7/007* (2013.01); *A61F 7/02* (2013.01); *A61G 7/05* (2013.01); *A61G 13/10* (2013.01); *A61F 2007/0004* (2013.01); *A61F 2007/0018* (2013.01); *A61F 2007/0036* (2013.01); *A61F 2007/0045* (2013.01); *A61F 2007/0054* (2013.01); *A61F 2007/0056* (2013.01); *A61F 2007/0093* (2013.01); *A61F 2007/0096* (2013.01); *A61F 2007/0233* (2013.01);
(Continued)

(58) Field of Classification Search
CPC ........ A61F 2007/0036; A61F 2007/004; A61F 7/007; A61F 7/02; A61F 2007/0018; A61F 2007/0045; A61F 2007/0093; A61F 2007/0004; A61F 2007/0006
See application file for complete search history.

(56) References Cited

U.S. PATENT DOCUMENTS

| 6,113,626 A | 9/2000 | Clifton et al. |
| 7,122,047 B2 | 10/2006 | Grahn et al. |

(Continued)

FOREIGN PATENT DOCUMENTS

WO    2013102056 A1    7/2013

OTHER PUBLICATIONS

International Preliminary Report on Patentability issued in corresponding PCT Application No. PCT/US2016/058492 dated May 3, 2018; 9pp.

(Continued)

*Primary Examiner* — Adam Z Minchella
(74) *Attorney, Agent, or Firm* — Studebaker & Brackett PC

(57) ABSTRACT

The described apparatuses, devices, and mechanisms are configured to measure the temperature of one or more Abreu brain thermal tunnel (ABTT) terminuses. In addition, some embodiments are configured to provide treatment for the diagnosed conditions and diseases.

19 Claims, 12 Drawing Sheets

Related U.S. Application Data

(60) Provisional application No. 62/245,010, filed on Oct. 22, 2015.

(51) Int. Cl.
*A61G 7/05* (2006.01)
*A61G 13/10* (2006.01)

(52) U.S. Cl.
CPC ...... *A61G 2203/46* (2013.01); *A61G 2210/70* (2013.01); *A61G 2210/90* (2013.01)

(56) References Cited

U.S. PATENT DOCUMENTS

| | | | |
|---|---|---|---|
| 7,187,960 | B2 | 3/2007 | Abreu |
| 9,456,948 | B1 | 10/2016 | Lazarof |
| 2003/0024684 | A1 | 2/2003 | Lyons et al. |
| 2003/0109910 | A1 | 6/2003 | Lachenbruch et al. |
| 2004/0249427 | A1 | 12/2004 | Nabilsi |
| 2005/0085882 | A1* | 4/2005 | Grahn ............ A61H 35/006 607/104 |
| 2006/0069418 | A1 | 3/2006 | Schock et al. |
| 2007/0112400 | A1 | 5/2007 | Hamilton et al. |
| 2007/0180625 | A1 | 8/2007 | Walke et al. |
| 2008/0077212 | A1 | 3/2008 | Hammac |
| 2008/0132816 | A1 | 6/2008 | Kane et al. |
| 2009/0099629 | A1 | 4/2009 | Carson et al. |
| 2009/0105605 | A1 | 4/2009 | Abreu |
| 2010/0191314 | A1 | 7/2010 | Young |
| 2011/0144209 | A1* | 6/2011 | Zachar ............ A61K 36/752 514/616 |
| 2011/0155795 | A1 | 6/2011 | James et al. |
| 2011/0195374 | A1 | 8/2011 | Boren |
| 2013/0305451 | A1 | 11/2013 | Asaf et al. |
| 2013/0317578 | A1* | 11/2013 | Diller ............ A61B 5/01 607/104 |
| 2014/0277308 | A1 | 9/2014 | Cronise et al. |
| 2015/0094914 | A1 | 4/2015 | Abreu |
| 2015/0105687 | A1 | 4/2015 | Abreu |
| 2015/0196203 | A1 | 7/2015 | Abreu |
| 2015/0202417 | A1 | 7/2015 | Abreu |
| 2015/0209174 | A1 | 7/2015 | Abreu |
| 2018/0125703 | A1 | 5/2018 | Diller |

OTHER PUBLICATIONS

International Search Report and Written Opinion issued in corresponding PCT Application No. PCT/US2016/058492 dated Jan. 3, 2017; 10pp.

* cited by examiner

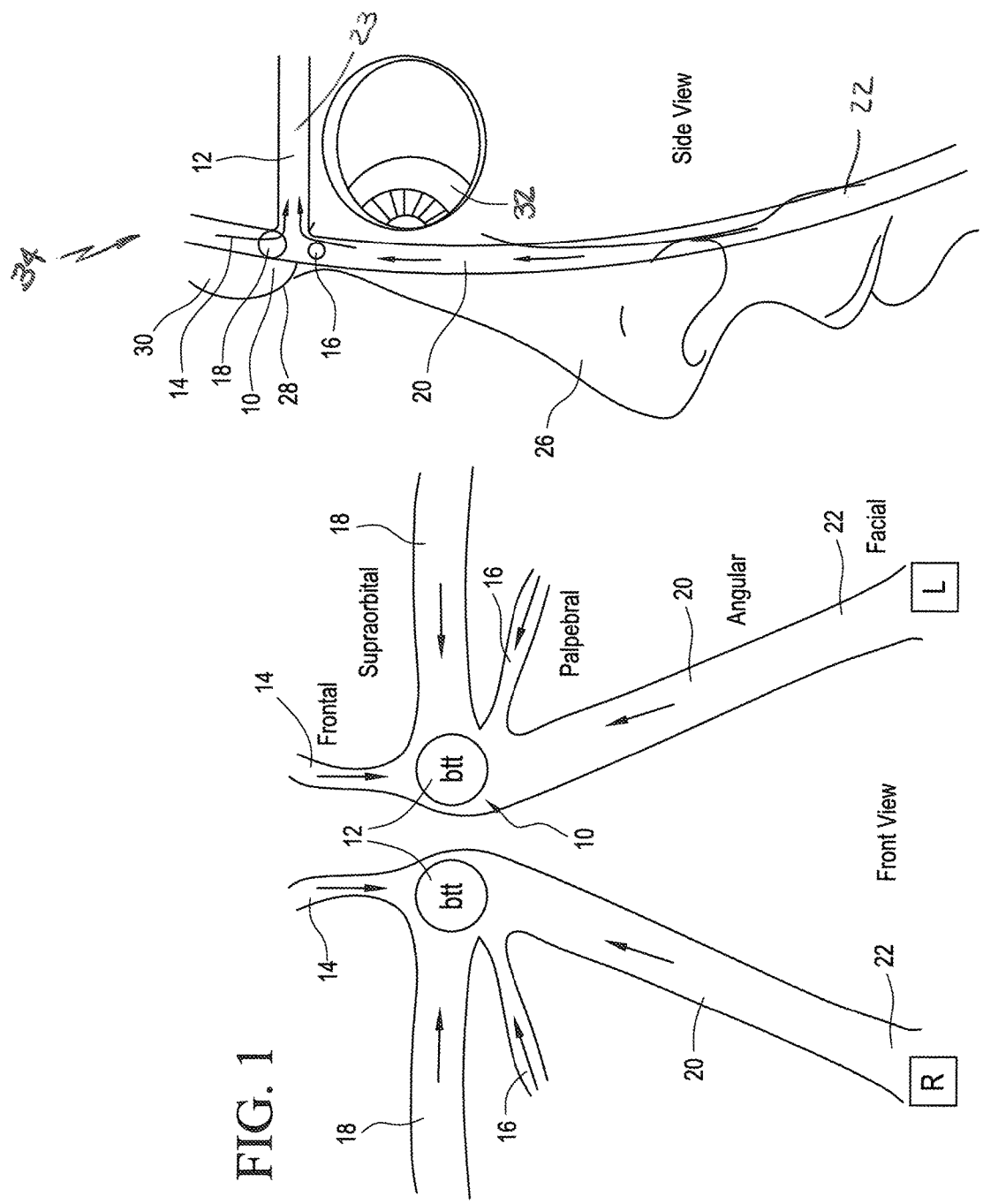

THERAPEUTIC BED OR GURNEY FOR THERMAL DIAGNOSIS AND TREATMENT OF A HUMAN

CROSS-REFERENCE TO RELATED APPLICATIONS

This application is a continuation of U.S. patent application Ser. No. 15/332,738, filed on Oct. 24, 2016, which claims the benefit of priority to U.S. Provisional Patent Application No. 62/245,010, filed on Oct. 22, 2015, which is hereby incorporated by reference in its entirety.

TECHNICAL FIELD

This disclosure relates to devices used to support a reclining human patient or subject, such as a bed or gurney. The bed or gurney is configured to provide a thermal diagnosis and therapeutic thermal treatment to the reclining human patient or subject. Such thermal diagnosis and treatment can include providing or removing heat from a patient or subject.

BACKGROUND

Hospital beds and gurneys are devices commonly used in hospitals and in medical transports, including airplanes, ambulances, rescue vehicles, helicopters, ships, etc. Such beds can support devices such as IV drips and electronic sensor panels. Thermal diagnosis includes the use of thermometers at various body locations and thermal treatment includes the use of blankets, HVAC, and ice.

SUMMARY

This disclosure provides a brain modification system comprising a horizontally-extending patient support device for supporting a patient, a plurality of temperature modification devices, at least one temperature sensor, and a processor. The plurality of temperature modification devices are positioned on the support device, including at least one temperature modification device positioned to provide heat to or to remove heat from a respective one of a plurality of extremities of the patient. Each of the plurality of temperature modification devices is formed of a flexible material. The at least one temperature sensor is sized and dimensioned to acquire a temperature measurement from an Abreu brain thermal tunnel (ABTT) terminus located between an eye and an eyebrow of the patient and is configured to transmit a signal representative of the temperature measurement. The processor is configured to control the plurality of temperature modification devices and configured to receive the signal from the at least one temperature sensor. The processor configured to determine from the signal a hypothermic or hyperthermic condition of the patient, to control the plurality of temperature modification devices to remove heat from at least one of the plurality of extremities when a hypothermic condition is determined, and to control the plurality of temperature modification devices to provide heat to at least one of the plurality of extremities when a hyperthermic condition is detected.

Advantages and features of the embodiments of this disclosure will become more apparent from the following detailed description of exemplary embodiments when viewed in conjunction with the accompanying drawings.

BRIEF DESCRIPTION OF THE DRAWINGS

FIG. 1 shows a simplified view of the Abreu brain thermal tunnel (ABTT) and facial veins associated with the ABTT.

FIG. 2 shows a simplified partial cross-sectional view through a human head in a vertical direction, showing the ABTT and certain other facial features.

DETAILED DESCRIPTION

The Abreu brain thermal tunnel (ABTT) provides a unique opportunity to diagnose an array of conditions and diseases that were previously difficult or even impossible to diagnose, and to treat those diseases and conditions, as disclosed by Applicant in co-pending U.S. patent application Ser. No. 14/512,421, filed on Oct. 11, 2014, Ser. No. 14/512,427, filed on Oct. 11, 2014, Ser. No. 14/593,848, filed on Jan. 9, 2015, Ser. No. 14/594,122, filed on Jan. 10, 2015, and Ser. No. 14/603,353, filed on Jan. 22, 2015, incorporated herein by reference in their entirety. The present disclosure provides beds and gurneys for the automatic diagnosis of conditions and diseases via a terminus of the ABTT and automatic thermal treatment of those conditions and diseases.

Diagnosis and treatment of human conditions, particularly conditions that affect the internal core and brain temperature of a human, such as hypothermia and hyperthermia, can be difficult to diagnose accurately. Even when such conditions can be diagnosed accurately, treatment of such conditions is challenging because it is relatively easy to cause a brain or organ temperature condition that leads to organ shutdown and death. The devices of the present disclosure provide improved systems and apparatuses that diagnose human thermal conditions by non-invasively measuring the internal or core temperature of a patient or subject, and modifying body temperature to restore internal or core temperature effectively while minimizing additional organ damage or without sending a body into shock leading to death.

Figure 3:
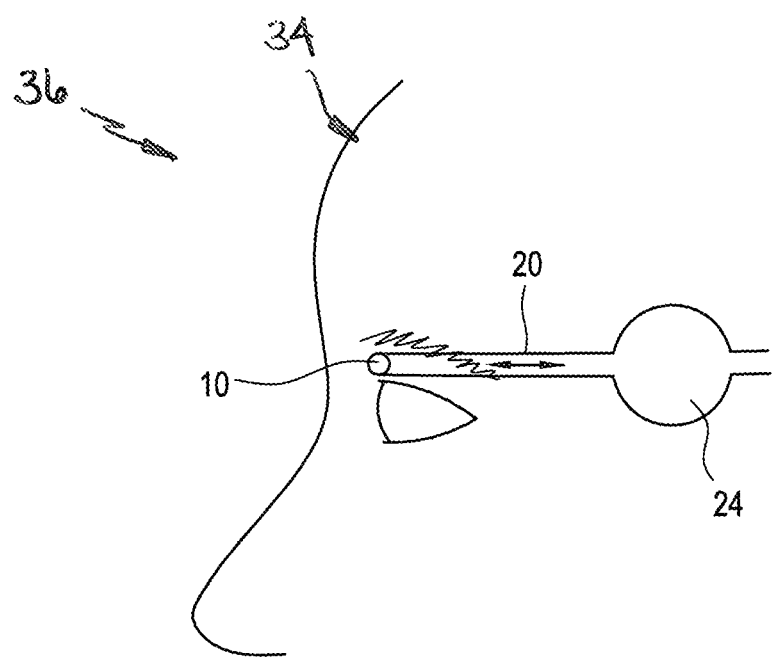
FIG. 3 shows a stylized representation of a flow of blood into and out from a brain core.

The present disclosure arises from the discovery that the Abreu brain thermal tunnel, or ABTT, provides the first known structure for brain-surface thermodynamic communication and thermal connection directly with the center of the brain. Anatomically and physiologically speaking, and as shown in FIGS. 1-3, ABTT 12 includes a continuous, direct, and undisturbed connection between a brain core 24 at the control center of the brain and the skin of ABTT terminus 10. The skin of ABTT terminus 10 is unique in that it is the thinnest skin with the fewest layers of any skin on a human body, it is absent a fat layer, and it has the high thermal conductivity of any skin on the human body.

The physical and physiological events at one end of the tunnel are reproduced at the opposite end. Thus, ABTT 12 enables the direct transfer of temperature signals from brain core 24 to ABTT terminus 10 without significant barriers, as described in co-pending U.S. patent application Ser. No. 14/512,421. Furthermore, modification of temperature at ABTT terminus 10, including application of heat and removal of heat, colloquially and conventionally described as cooling, applying cold, and the like, directly affects brain core 24, and ultimately, the entire body of the patient or subject. Accordingly, the present disclosure includes descriptions of apparatuses for acquiring temperature signals from ABTT terminus 10, analyzing those signals, and determining a human condition from those signals. In addition, apparatuses for the treatment of human conditions can be combined with temperature acquisition apparatuses, as disclosed herein.

Anatomy shows the convergence of four veins at ABTT target area 10: frontal 14, superior palpebral 16, supraorbital 18, and angular 20. As angular vein 20 extends further from ABTT 12, it transitions into facial vein 22. Having converged, there is a direct, valve-free connection from ABTT terminus or target area 10 between an eye 32 and an eyebrow 28 into the center of the brain, i.e., brain core 24, which is the temperature center present in the hypothalamus or thermal storage area of the body present in the cavernous sinus.

FIGS. 1 and 2 show the approximate location of these veins in relation to other facial features. Angular/facial vein 20/22 runs up alongside nose 26, superior palpebral vein 16 runs along eyebrow 28, and frontal vein 14 and supraorbital vein 18 run through forehead 30, all positioned on a head 34. For the purposes of disclosure, terminology referring to relevant facial areas or veins herein will be described as one or more of the above-referenced veins and ABTT target area 10.

As described herein, veins 14, 16, 18, 20, and 22 converge in the superomedial orbit in the region of the upper eyelid and adjacent to the bridge of the nose, and flow directly, without inhibition, to the center of the brain. The skin in this area, as shown in applications by Applicant, is the thinnest skin in the body and free of fat, providing an unexpectedly rapid communication of temperature from the brain core to the skin of ABTT terminus 10. These vessels lack valves, which are typically an important barrier to blood flow and the direct and rapid transmission of temperature signals. Without valves, these blood vessels truly provide a direct, uninhibited passage for transporting temperature signals directly to and from the hypothalamic region of the brain. Moreover, ABTT 12 includes a superior ophthalmic vein (SOV) 23, which connects the skin surface to the brain and corresponds to the central portion of the tunnel (ABTT 12), is valveless, and has bidirectional blood flow. The SOV lies directly underneath the skin of the superomedial orbit, between eye 32 and eyebrow 28, and is a direct conduit from the surface of the skin at the facial end of ABTT 12, i.e., ABTT terminus 10, to the brain, and then to the hypothalamus. The hypothalamic region of the brain is the link between the central nervous system and the endocrine system and, as such, acts as the center of control for many basic bodily functions such as, for example, hunger, thirst, body temperature, fatigue, blood pressure, immune responses, circadian cycles, hormone production and secretion, and many others.

The facial end of ABTT 12, herein referred to as a target area, or terminus 10 on the skin on, over, or adjacent to ABTT 12, measures about 11 mm in diameter measured from the medial corner of eye 32 at the medial canthal tendon and extends superiorly for about an additional 6 or 7 mm in an ABTT superior projection 11, and then extends into an upper eyelid in a horn-like projection 13 for another 22 mm. ABTT terminus 10 is absent fat, and a ABTT superior projection and a horn-like projection are absent fat in areas near to ABTT terminus 10, with a fat layer present in areas a spaced distance away from ABTT terminus 10.

Figure 4:
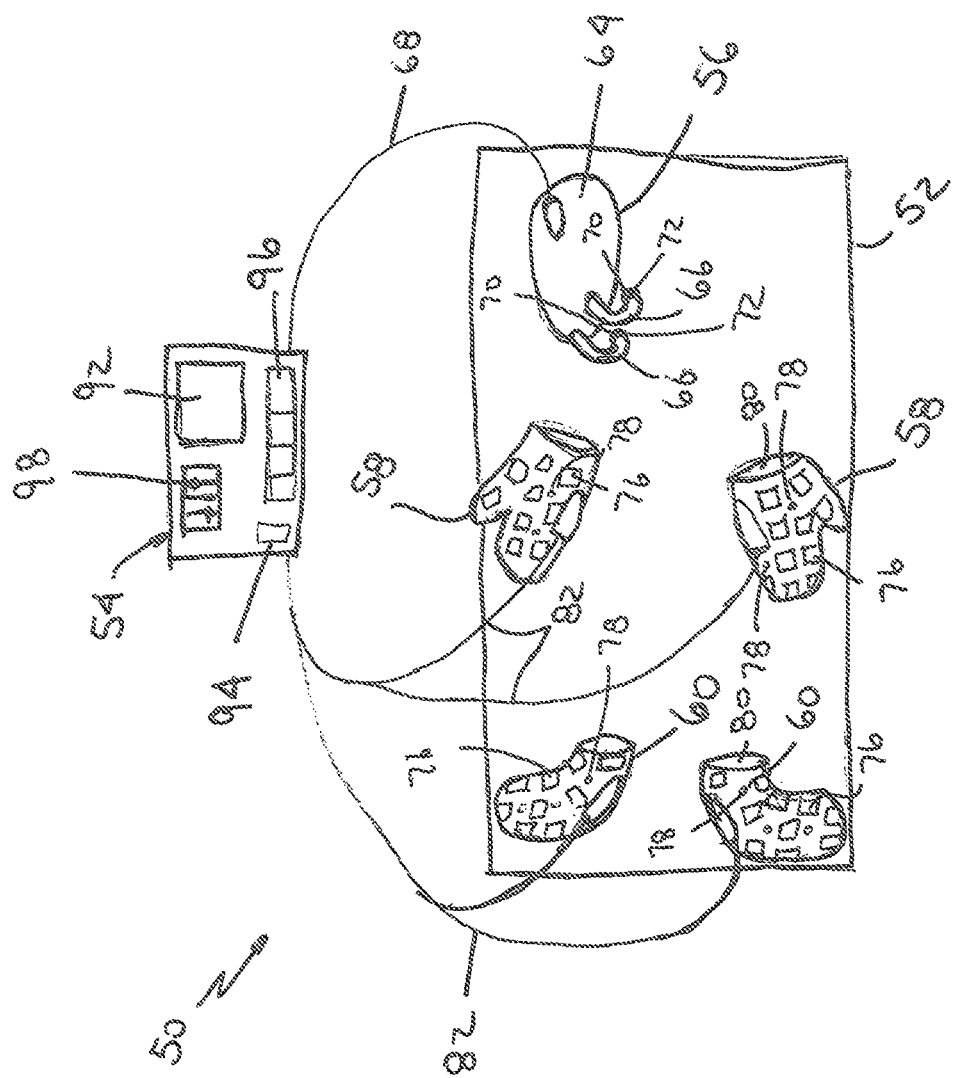
FIG. 4 shows a plan view of a thermal diagnosis and therapeutic system in accordance with an exemplary embodiment of the present disclosure.

FIG. 4 shows a plan view of a thermal diagnosis and therapeutic system 50 in accordance with an exemplary embodiment of the present disclosure. System 50 includes many of the basic elements needed to diagnose thermal conditions of a human subject or patient 36 automatically, while supporting subject or patient 36. System 50 includes a bed 52, a controller 54, a headgear 56, and extremity interfaces, such as hand interfaces, mittens, or gloves 58 and foot interfaces or booties 60.

Bed 52 extends generally in a horizontal direction functions to support a patient or subject (not shown in FIG. 4).

Figure 6:
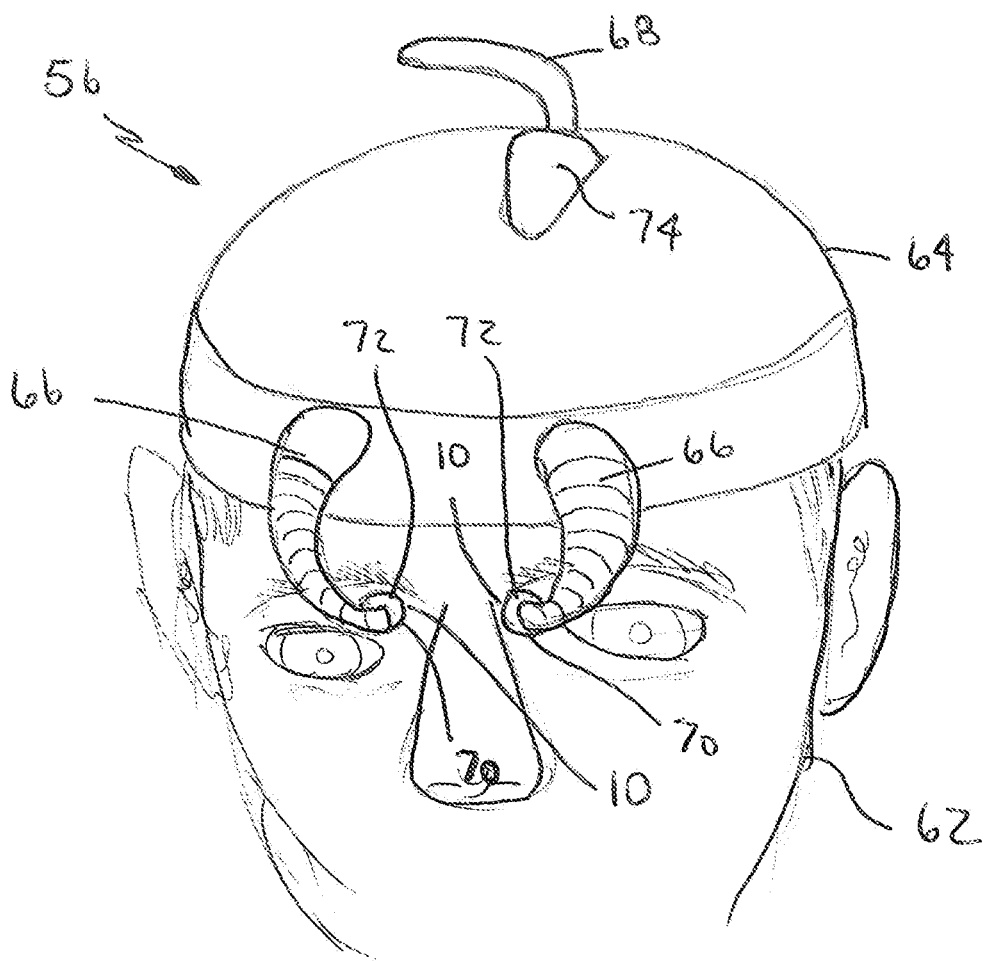
FIG. 6 shows a plan view of another thermal diagnosis and therapeutic system in accordance with an exemplary embodiment of the present disclosure.

Headgear 56, also shown in FIG. 6, is configured to be positioned on and supported by head 34 of a patient or subject 62. Headgear 56 includes a support portion or cap 64, and one or more adjustable arms 66 supported by support portion 64. Adjustable arms 66 may also be described as flexible arms. Support portion or cap 64 can be adjustable to provide a proper fit to various head sizes. Headgear 56 is connected to controller 54 by one or more cables or wires 68, which connects power from controller 54 to elements of headgear 56, and which connects signals from elements of headgear 56 to controller 54. It should be understood that control signals transmitted to headgear 54 and signals from headgear 54 can be transmitted or received wirelessly.

Each adjustable arm 66 includes at least a temperature sensor 70 positioned on or near an end of adjustable arm 66. Each adjustable arm 66 may also include a heating or cooling device, such as a thermoelectric device 72. Each temperature sensor 70 is sized and dimensioned to interface with an ABTT terminus 10 to acquire a temperature measurement from ABTT terminus 10. Wires (not shown) run through support portion 64 and through adjustable arms 66 to provide power from cable or wire 68 to thermoelectric devices 72 and to provide signals representative of temperature from temperature sensors 70 to cable or wire 68. In an exemplary embodiment, wires from cable or wire 68 extend through adjustable arms 66 to connect to temperature sensors 70 and thermoelectric devices 72. In another exemplary embodiment, cable or wire 68 attaches to a connector 74, and wires extend from connector 74 to temperature sensors 70 and thermoelectric devices 72.

After headgear 56 is positioned on the head of patient or subject 62, each temperature sensor 70 is positioned on, near, adjacent, or alongside a respective ABTT terminus 10 by adjusting the position of each adjustable arm 66. The proximity of thermoelectric devices 72 to temperature sensor 70 also positions each thermoelectric device 72 in an area near a respective ABTT terminus 10. It should be understood that it is preferable for temperature sensors 70 and thermoelectric devices 72 to be in direct contact with ABTT terminus 10 for maximum transfer of heat to and from temperature sensor 70 and thermoelectric devices 72. However, it is contemplated that a temperature modification device and/or temperature sensing device can be positioned a spaced distance from ABTT terminus 10. For example, an infrared light sensor can detect infrared light or radiation that can be correlated to a temperature of ABTT terminus 10 without contacting ABTT terminus 10. Though not shown, additional temperature modification devices can be positioned to provide hit to or remove hit from the skin over veins 14, 16, 18, 20, and 22 as long as skin on the rest of the face is not affected by the additional temperature modification devices to avoid stimulation of facial thermal receptors.

Each hand interface 58 and each foot interface 60 includes heating and/or cooling elements, such as thermoelectric devices 76, and one or more temperature sensors 78, and thus hand interfaces 58 and foot interfaces 60 function as temperature modification devices. Temperature sensors 78 terminate at or near an interior surface 80 of a respective hand interface 58 or a respective foot interface 60 to provide temperature measurements of the skin of a foot or a hand. Each hand interface 58 and each foot interface 60 can be formed of a flexible or compliant material for better conformance of hand interface 58 and foot interface 60 to an associated hand or foot.

Each hand interface 58 and each foot interface 60 is connected to controller 54 by a cable or wire 82. Cable or wire 82 connects power supplied by controller 54 to thermoelectric devices 76, and connects signals from temperature sensors 78 to controller 54, though signals, such as signals from temperature sensors 78, can also be transmitted from hand interfaces 58 and foot interfaces 60 wirelessly, as well as any control signals to hand interfaces 58 and foot interfaces 60 that may be transmitted by controller 54.

Figure 5:
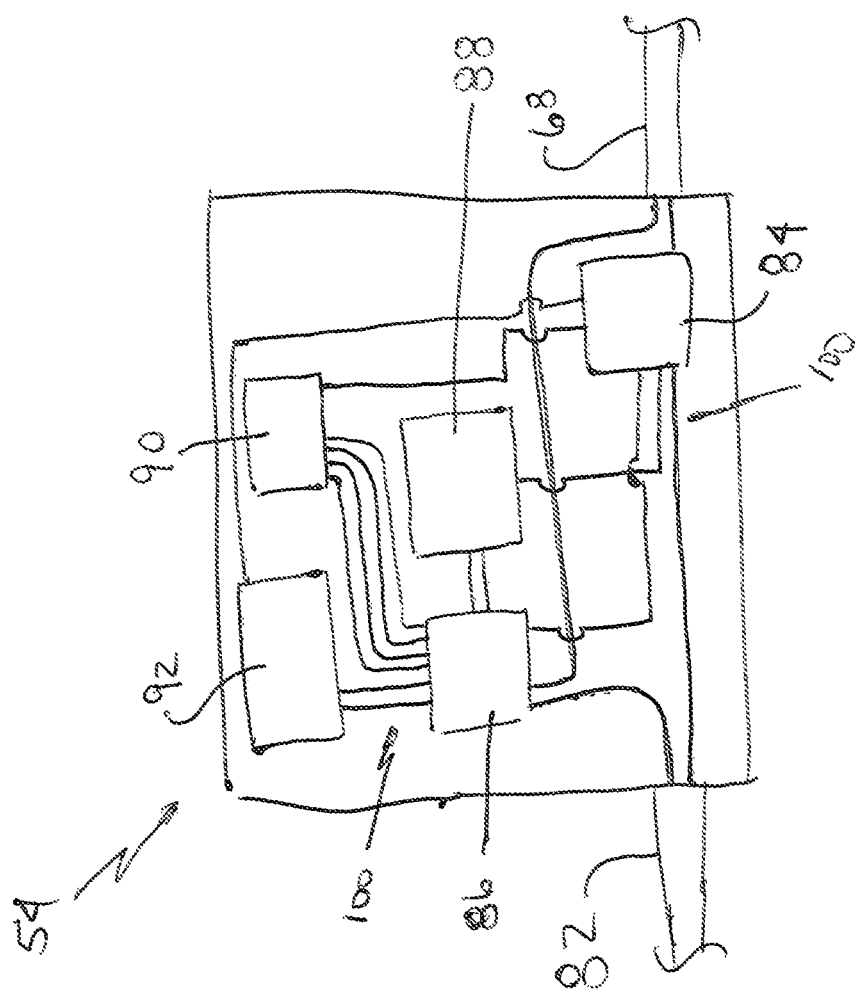
FIG. 5 shows a block diagram view of a controller in accordance with an exemplary embodiment of the present disclosure.

Referring to FIGS. 4 and 5, controller 54 includes a power supply 84, a physical processor 86 (e.g., a CPU), a non-transitory memory 88, an input module 90, and a display 92. Input module 90 can include a plurality of controls, such as buttons and switches, which can include an ON/OFF button or switch 94, various buttons and switches 96 configured to control the operation of controller 54, and increment/decrement controls 98 that control increase and decrease in temperature of thermoelectric devices 76. It should be understood that while separate physical switches are shown in the exemplary embodiment of FIG. 4, such switches may be soft switches accessed by a touch screen of display 92, or other types of control input.

Power supply 84 can be energized by ON/OFF switch 94, which then provides power to processor 86, non-transitory memory 88, though such power to non-transitory memory 88 can be via processor 86, input module 90, and display 92. Once the internal elements of controller 54 are powered, processor 86 will proceed through a startup process, during which software from non-transitory memory 88 or from firmware will be accessed by processor 86 to prepare thermal diagnosis and therapeutic system 50 for operation.

Either before or after system 50 is initialized, an operator can position headgear 56 on the head of a patient or subject, such as patient or subject 62, and then position adjustable arms 66 such that at least one temperature sensor 70 contacts a respective ABTT terminus 10. The operator further positions hand interfaces 58 and foot interfaces 60 on the hands and feet, respectively, of patient or subject 62. After positioning headgear 56, hand interfaces 58, and foot interfaces 60, buttons and switches 96 can be actuated, sending signals to input module 90 to operate controller 54 to receive or acquire signals representing temperature information from at least one temperature sensor 70. In an exemplary embodiment, controller 54 can be operated to receive or acquire signals representing temperature from a plurality of temperature sensors 78 positioned on hand interfaces 58 and foot interfaces 60. As described in more detail below, in an exemplary embodiment, controller 54 can automatically control the operation of thermoelectric devices 76, or thermoelectric devices 76 can be manually controlled by, for example, increment/decrement controls 98, which send signals to input module 90.

It should be understood that signals received or generated by input module 90 are provided to processor 86 in an exemplary embodiment. However, input module 90 may also directly control some elements of controller 54, such as certain functions of display 92. It should also be understood that the various elements of controller 54 are connected to each other by various interconnections 100, which may be configured as a wire harness.

System 50 can operate to diagnose a thermal condition of a patient by measuring the temperature of ABTT terminus 10 because, as explained hereinabove, ABTT terminus 10 provides an accurate representation of the temperature of brain core 24, which is also representative of the core temperature of the body. For example, if patient or subject 62 is hypothermic, the temperature of ABTT terminus 10 will be below the normal temperature range for humans. For example, hypothermia can be defined as a core temperature below 95 degrees Fahrenheit.

When system 50 detects a hypothermic condition, system 50 is configured to provide two responses. First, heat that is greater than 95 degrees Fahrenheit can be immediately provided to at least one ABTT terminus 10. For example, heat that is 1-3 degrees Fahrenheit greater than the measured temperature of ABTT terminus 10 can be applied directly to at least one ABTT terminus 10. Second, an increased temperature can be applied to hands and feet via or by way of hand interfaces 58 and foot interfaces 60, though at a temperature that remains substantially lower than core temperature.

For example, an exemplary temperature applied to the extremities should be no more than 1 degree Fahrenheit greater than the skin temperature of the extremities. The reason for limiting the temperature increase to the extremities is that the extremities contain numerous thermal receptors, and the brain can consider excessive heat applied to the extremities as a signal that the body is becoming too cold, which then causes the brain to respond by cooling the body core in anticipation of warm temperatures. Such cooling makes hypothermia worse, and can lead to shock, organ damage, and organ shut down, potentially leading to death. However, by maintaining a temperature of hand interfaces 58 and foot interfaces 60 near the skin temperature of the extremities of a hypothermic patient or subject, though slightly elevated, such as by about one degree Fahrenheit, the brain perceives the temperature of the extremities to be cold, and the brain responds by drawing heat from any available source, which includes heat applied to ABTT terminus 10. The heat applied to ABTT terminus 10 is drawn directly through ABTT 12 into brain core 24, which rapidly raises the temperature of the brain, which improves in function as it warms so that it can then further control the function of other elements of the body to raise body core temperature, quickly alleviating a hypothermic condition.

When system 50 detects a hyperthermic condition, system 50 is configured to provide two responses, similar to detection of a hypothermic condition. However, the responses in this situation are opposite the responses for hypothermia. First, cooling that is less than the measured temperature of ABTT terminus 10 can be immediately provided to at least one ABTT terminus 10. For example, heat that is 1-3 degrees Fahrenheit lower than the measured temperature of ABTT terminus 10 can be applied directly to at least one ABTT terminus 10. Second, an increased temperature can be applied to hands and feet via or by way of hand interfaces 58 and foot interfaces 60, though at a temperature that remains substantially lower than core temperature. Activation of thermal receptors in the hands and feet by an elevated temperature is perceived by the brain as an impending increase in environmental temperature. The brain responds to this perception by decreasing the temperature of the brain, thus cooling the brain and alleviating the hyperthermic condition.

Figure 7:
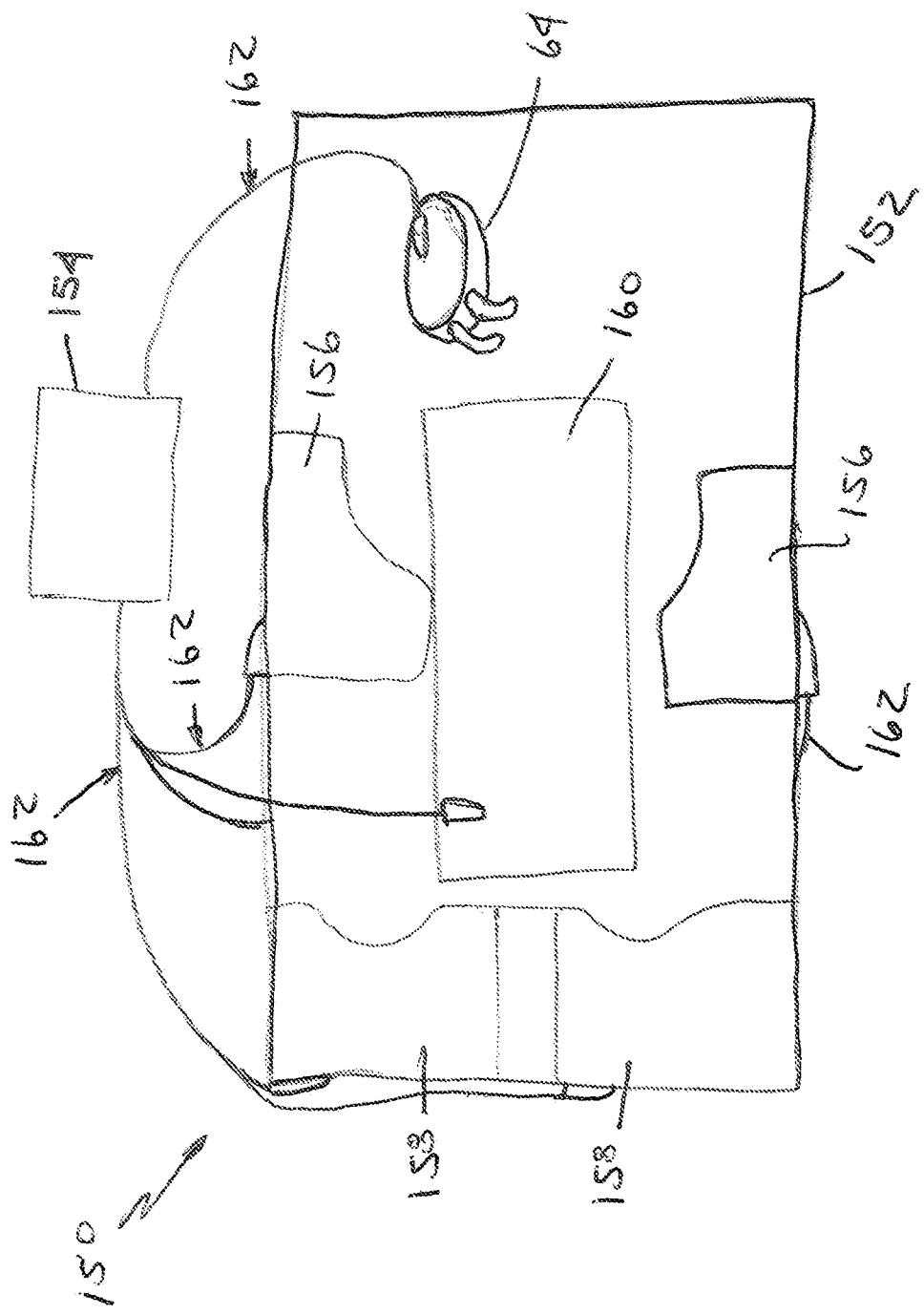
FIG. 7 shows a headgear compatible with the thermal diagnosis and therapeutic systems of the present disclosure in accordance with an exemplary embodiment of the present disclosure.

FIG. 7 shows a plan view of another thermal diagnosis and therapeutic system 150 in accordance with an exemplary embodiment of the present disclosure. System 150 includes a bed 152, a controller 154, a plurality of hand interfaces 156, a plurality of foot interfaces 158, a torso interface 160, headgear 64, and a cable/wiring harness 162 for connecting the various elements of system 150 to each other.

Hand interfaces 156, foot interfaces 158, and torso interface 160 each function as temperature modification devices for warming or cooling of hands, feet, and torso of a subject, user, or patient. Each of hand interfaces 156, foot interfaces 158, and torso interface 160 can include thermoelectric devices to provide heating and cooling, or other devices that preferably have the ability to heat and cool. Torso interface 160 is generally sized and dimensioned to provide heat or remove heat, i.e., cool, only a torso of a patient, though portions of arms, legs, and neck can be warmed or cooled, as long as torso interface 160 is positioned away from the extremities.

Bed 152 can be a modified hospital bed. Controller 154 can be similar to controller 54 shown in FIGS. 4 and 5, though with the ability to separately control temperature modification device 160. Headgear 64 can be the headgear described hereinabove and shown in FIGS. 4 and 6.

To maximize effectiveness of cooling or warming brain core 24, the extremities, i.e., the hands and the feet, are cooled by hand interfaces 156 and foot interfaces 158 for hypothermic conditions, and are warmed by hand interfaces 156 and foot interfaces 158 for hyperthermic conditions, while the torso is warmed for hypothermic conditions and is cooled for hyperthermic conditions. Because the brain believes that cool ambient temperatures exist when the extremities are cooled, as indicated to the brain by thermal receptors in the hands and/or feet, the brain moves heat from other regions of the body, especially the warmed or heated torso, to critical areas, such as brain core 24 and other internal organs, alleviating a hypothermic condition. Similarly, when the brain believes warm temperatures are present when the extremities are warmed, as indicated to the brain by thermal receptors in the hands and/or feet, the brain moves cooler blood from the cooled torso to brain core 24 and other internal organs. Thus, system 150 is able to take advantage of the brain's use of thermal sensors in the extremities to direct heated or cooled blood from the torso to critical areas of the body.

Figure 8:
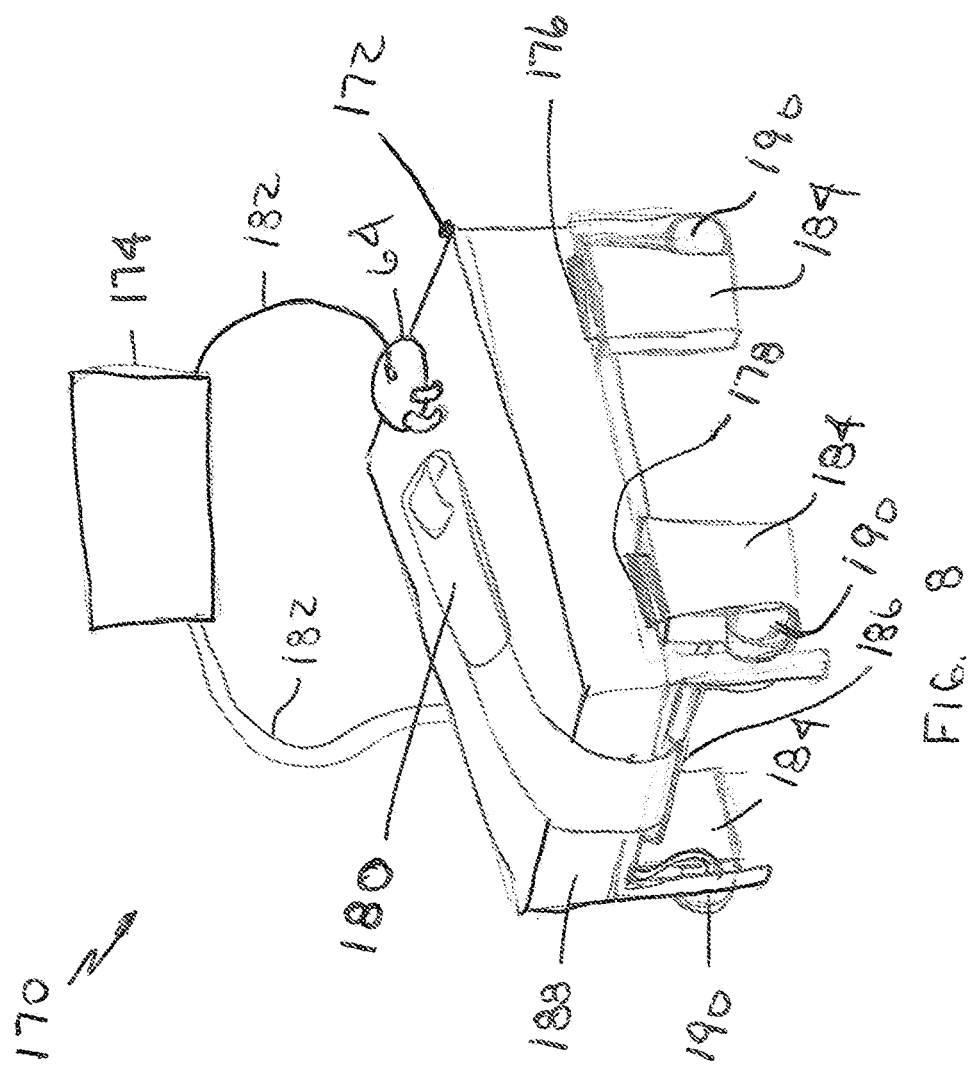
FIG. 8 shows a perspective view of yet another thermal diagnosis and therapeutic system in accordance with an exemplary embodiment of the present disclosure.

FIG. 8 shows a perspective view of yet another thermal diagnosis and therapeutic system 170 in accordance with an exemplary embodiment of the present disclosure. System 170 is functionally similar to system 150 shown in FIG. 7, and includes a bed 172, a controller 174, a plurality of hand interfaces 176, a plurality of foot interfaces 178, a torso interface 180, headgear 64, and a cable/wiring harness 182 for connecting the various elements of system 170 to each other.

Hand interfaces 176, foot interfaces 178, and torso interface 180 each function as temperature modification devices for warming or cooling of hands, feet, and torso of a subject, user, or patient. Each of hand interfaces 176, foot interfaces 178, and torso interface 180 can include thermoelectric devices to provide heating and cooling, or other devices that preferably have the ability to heat and cool.

Bed 172 can be a modified hospital bed. Controller 174 can be similar to controller 154 shown in FIG. 7. Headgear 64 can be the headgear described hereinabove and shown in FIGS. 4 and 6.

System 170 includes a plurality of storage locations receptacles 184 positioned and supported on bed 172 for storage of hand interfaces 176 and foot interfaces 178 when interfaces 176 and 178 are not in use. System 170 further includes a storage receptacle 186 at least partially positioned on an underside of a mattress 188 for storage of torso interface 180 for storage of torso interface 180 when interface 180 is not in use. Each temperature modification device 176, 178, and 180 is attached to a retraction mechanism 190, which can be supported on a respective storage receptacle 184 and 186 or on bed 172. Retraction mechanism 190 can be, for example, a spring-loaded torsion winding mechanism, a weighted end, a motor, etc.

Figure 9:
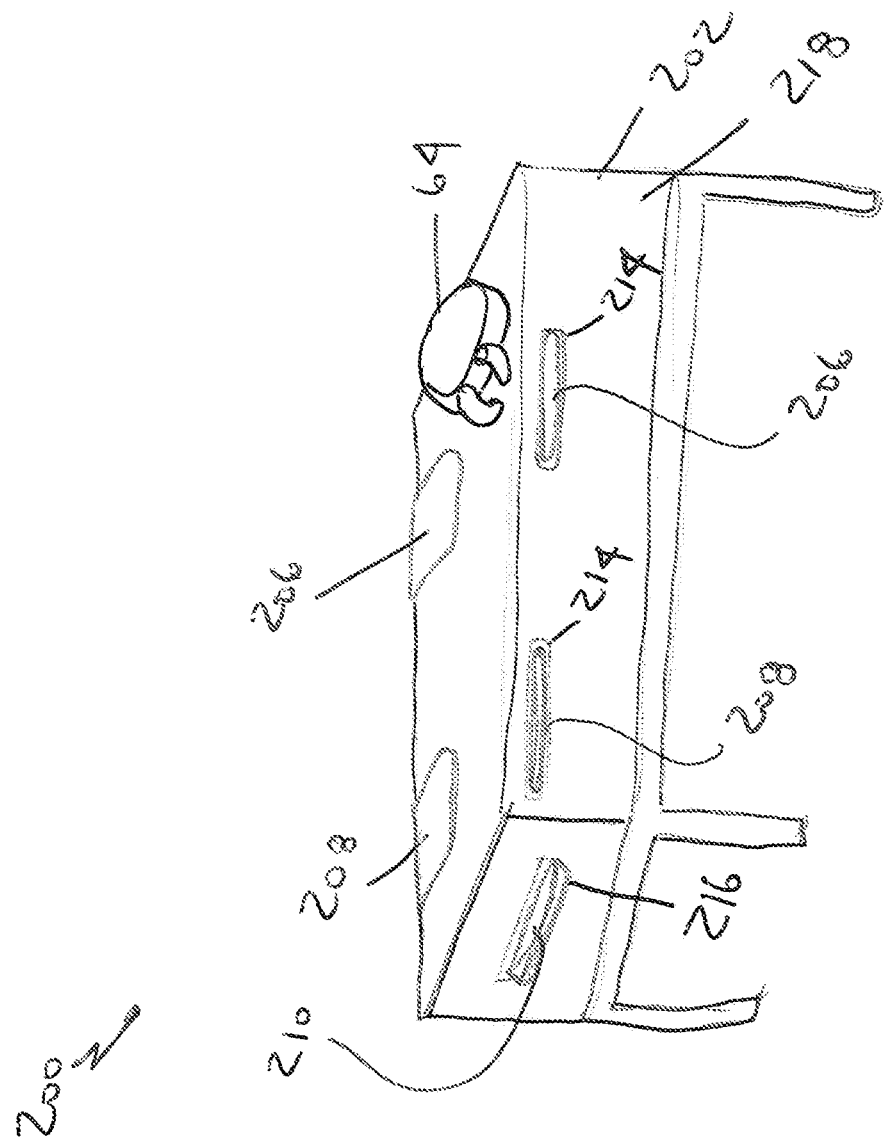
FIG. 9 shows a perspective view of a portion of a thermal diagnosis and therapeutic system in accordance with an exemplary embodiment of the present disclosure.

FIG. 9 shows a perspective view of a portion of a thermal diagnosis and therapeutic system 200 in accordance with an exemplary embodiment of the present disclosure. System 200 is functionally similar to system 150 shown in FIG. 7, and includes a bed 202, a controller (not shown), a plurality of hand interfaces 206, a plurality of foot interfaces 208, a torso interface 210, headgear 64, and a cable/wiring harness (not shown) for connecting the various elements of system 170 to each other.

Hand interfaces 206, foot interfaces 208, and torso interface 210 each function as temperature modification devices for warming or cooling of hands, feet, and torso of a subject, user, or patient. Each of hand interfaces 206, foot interfaces 208, and torso interface 210 can include thermoelectric devices to provide heating and cooling, or other devices that preferably have the ability to heat and cool.

Bed 202 can be a modified hospital bed. Headgear 64 can be the headgear described hereinabove and shown in FIGS. 4 and 6.

System 200 includes a plurality of storage receptacles 214 and 216 that are positioned and supported on bed 202 for storage of hand interfaces 206 and foot interfaces 208 when interfaces 206 and 208 are not in use. Each storage receptacle 214 and 216 is integrally positioned within a portion of bed 202, such as a frame portion, a mattress support, or a mattress 218. Each temperature modification device 206, 208, and 210 can be attached to a retraction mechanism (not shown) supported by bed 202. The retraction mechanism can be, for example, a spring-loaded torsion winding mechanism, a weighted end, a motor, etc.

One hand interface 206 and one foot interface 208 is shown extended in FIG. 9, with all other interfaces shown retracted for storage into bed 202 when not in use.

Figure 10:
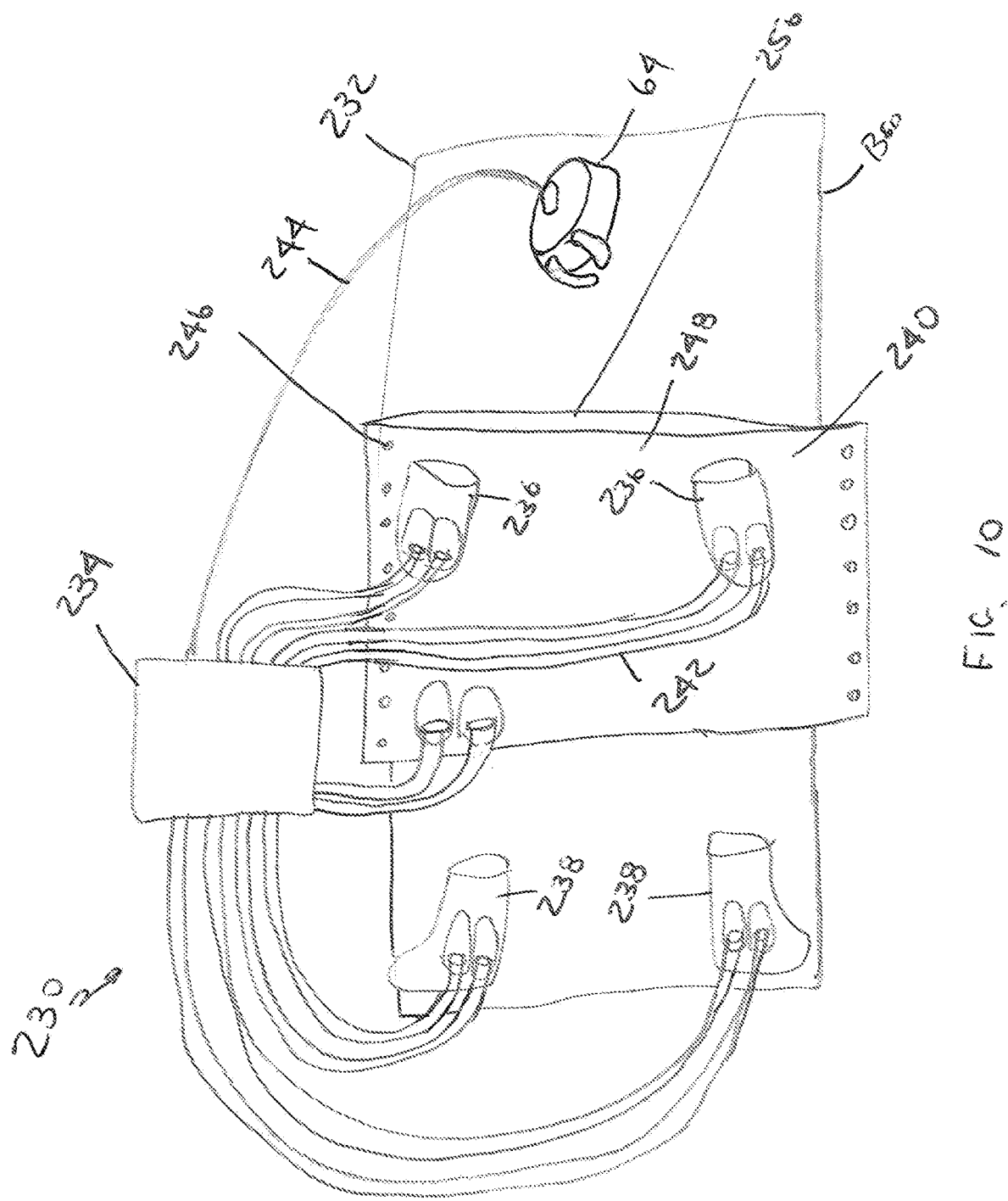
FIG. 10 shows a plan view of yet a further thermal diagnosis and therapeutic system in accordance with an exemplary embodiment of the present disclosure.

FIG. 10 shows a perspective view of yet another thermal diagnosis and therapeutic system 230 in accordance with an exemplary embodiment of the present disclosure. System 230 is functionally similar to system 150 shown in FIG. 7, and includes a bed 232, a controller 234, a plurality of hand interfaces 236, a plurality of foot interfaces 238, a torso interface 240, a plurality of fluid hoses, tubes, or lines 242, headgear 64, and a cable/wiring harness 244 for connecting the various electrical elements of system 230 to each other.

Hand interfaces 236, foot interfaces 238, and torso interface 240 each function as temperature modification devices for warming or cooling of hands, feet, and torso of a subject, user, or patient. Each of hand interfaces 236, foot interfaces 238, and torso interface 240 is warmed or cooled by temperature controlled fluid provided by way of fluid lines 242. The temperature controlled fluid is cooled or warmed by a separate chiller/heater unit that can be a separate element or can be part of controller 234.

Bed 232 can be a modified hospital bed. Controller 234 can include elements similar to controller 154 shown in FIG. 7 to interface with headgear 64, along with additional control devices for controlling the flow of fluid through fluid lines 242, and for controlling the temperature of fluid flowing through fluid lines 242. Headgear 64 can be the headgear described hereinabove and shown in FIGS. 4 and 6.

Hand interfaces 236 can be configured as mittens, and foot interfaces 238 can be configured as booties. Torso interface 240 is secured either to bedding or to bed 232 by fasteners 246, such as snaps. The advantage to this system is that it is readily adaptable to any conventional hospital bed with little or no modification to the bed. Note that torso temperature modification device 240 can include an upper portion 248 and a lower portion 250 to form a pocket for a patient or subject's torso; in this arrangement fasteners 246 can secure upper portion 248 to lower portion 250.

Figure 11:
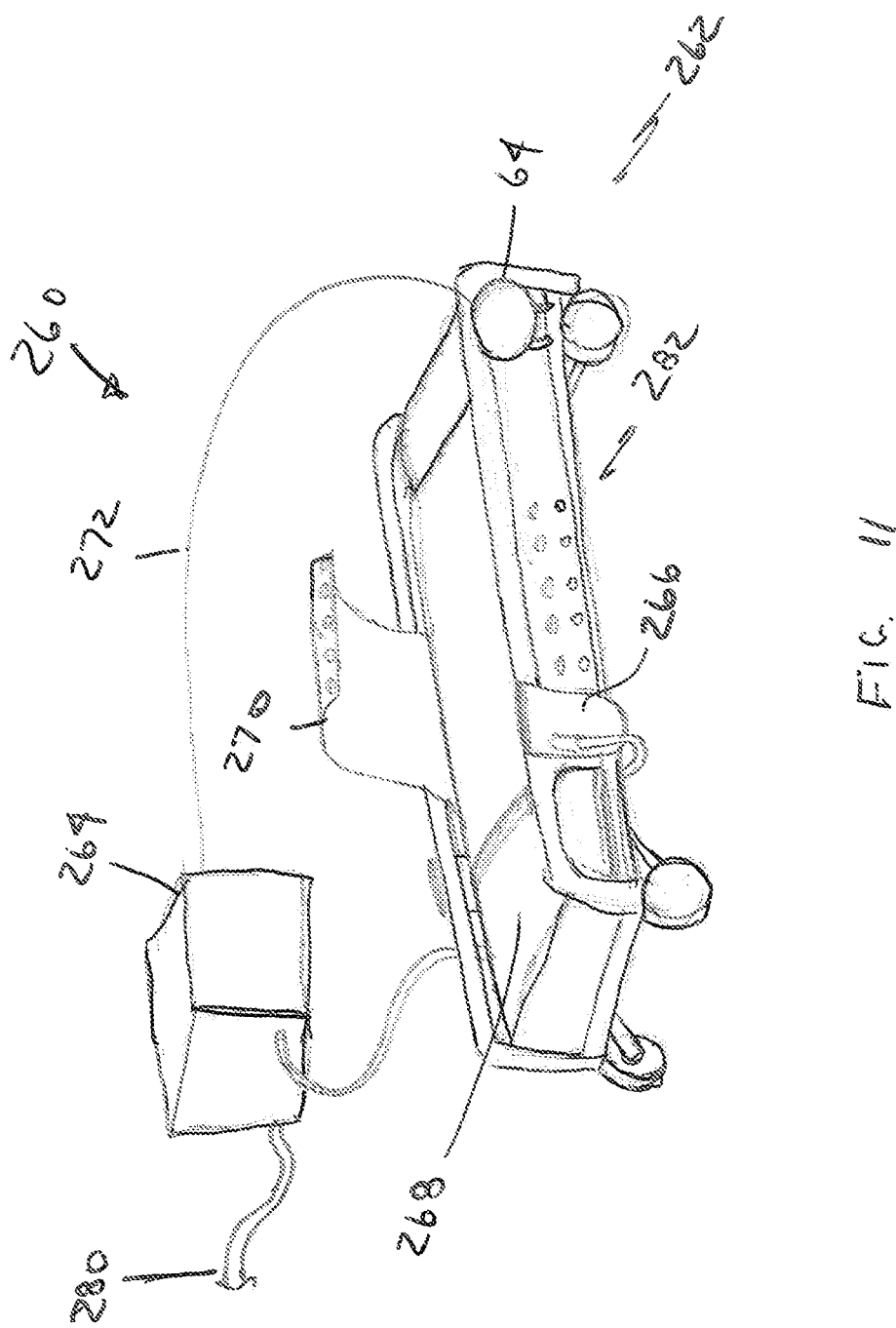
FIG. 11 shows a perspective view of still another thermal diagnosis and therapeutic system in accordance with an exemplary embodiment of the present disclosure.

FIG. 11 shows a perspective view of yet another thermal diagnosis and therapeutic system 260 in accordance with an exemplary embodiment of the present disclosure. System 260 is functionally similar to system 150 shown in FIG. 7, and includes a gurney 262, a controller 264, a plurality of hand interfaces 266, at least one foot interface 268, a torso interface 270, headgear 64, and a cable/wiring harness 272 for connecting the various elements of system 260 to each other.

Hand interfaces 266, at least one foot interfaces 268, and torso interface 270 each function as temperature modification devices for warming or cooling of hands, feet, and torso of a subject, user, or patient. Each of hand interfaces 266, foot interface 268, and torso interface 270 can include thermoelectric devices to provide heating and cooling, or other devices that preferably have the ability to heat and cool.

Gurney 262 can be a modified hospital gurney that provides attachment positions or storage locations for hand interfaces 266 and headgear 64. Controller 264 can be similar to controller 154 shown in FIG. 7 and can be powered from an external power source by way of power cable 280. Headgear 64 can be the headgear described hereinabove and shown in FIGS. 4 and 6. Temperature modification device 270 can be attached to gurney 262 by fasteners 282. Multiple rows of fasteners 282 can be provided to make the torso warmer/cooler and/or adjustable for different sized patients, or a retraction/tightening mechanism (not shown) can be loosened or tightened for different size patients. The system of FIG. 11 is powered by a vehicle power system, batteries, or locally available power by way of power cable 280.

Figure 12:
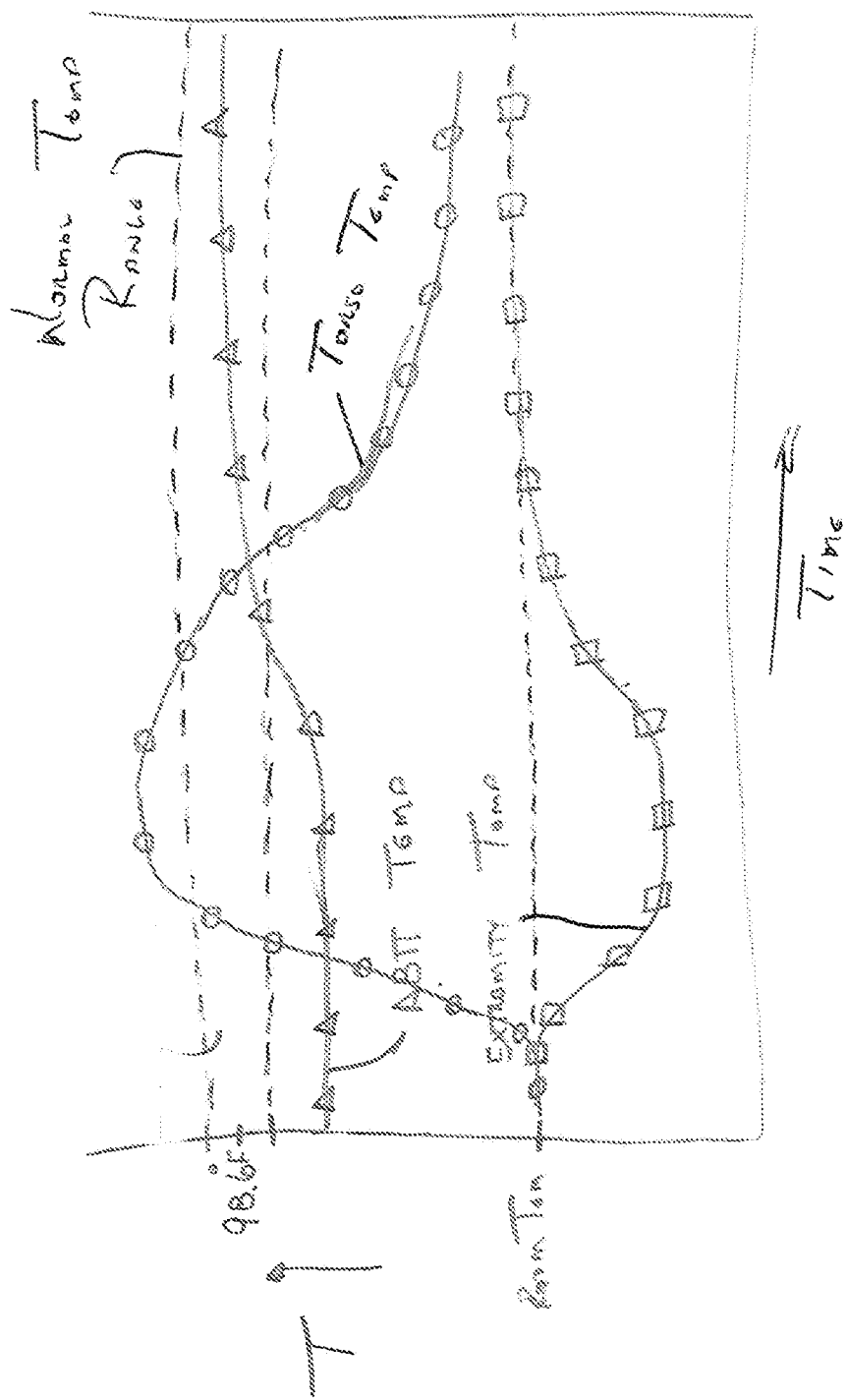
FIG. 12 shows an exemplary graph of representative temperatures for treatment of a hypothermic patient or subject.

FIG. 12 shows an exemplary graph of representative temperatures for treatment of a hypothermic patient or subject. An exemplary system determines core temperature via ABTT terminus 10. Once the hypothermic condition is determined, an exemplary system begins heating/cooling the extremities and torso, though opposite to each other (extremities heated, torso cooled) to cause the brain to move warmer torso blood to cool internal organs and brain core 24. The torso temperature is slowly and steadily increased to a predetermined maximum temperature while the extremities are cooled to a predetermined minimum temperature. Cooling and warming at a maximum predetermined rate, such as 0.5 degrees Fahrenheit per minute, reduces the risk of shock. As the ABTT temperature increases into a normal range, extremity cooling is slowly reduced while torso heating is similarly slowly reduced until normal temperatures are obtained and are stable.

Figure 13:
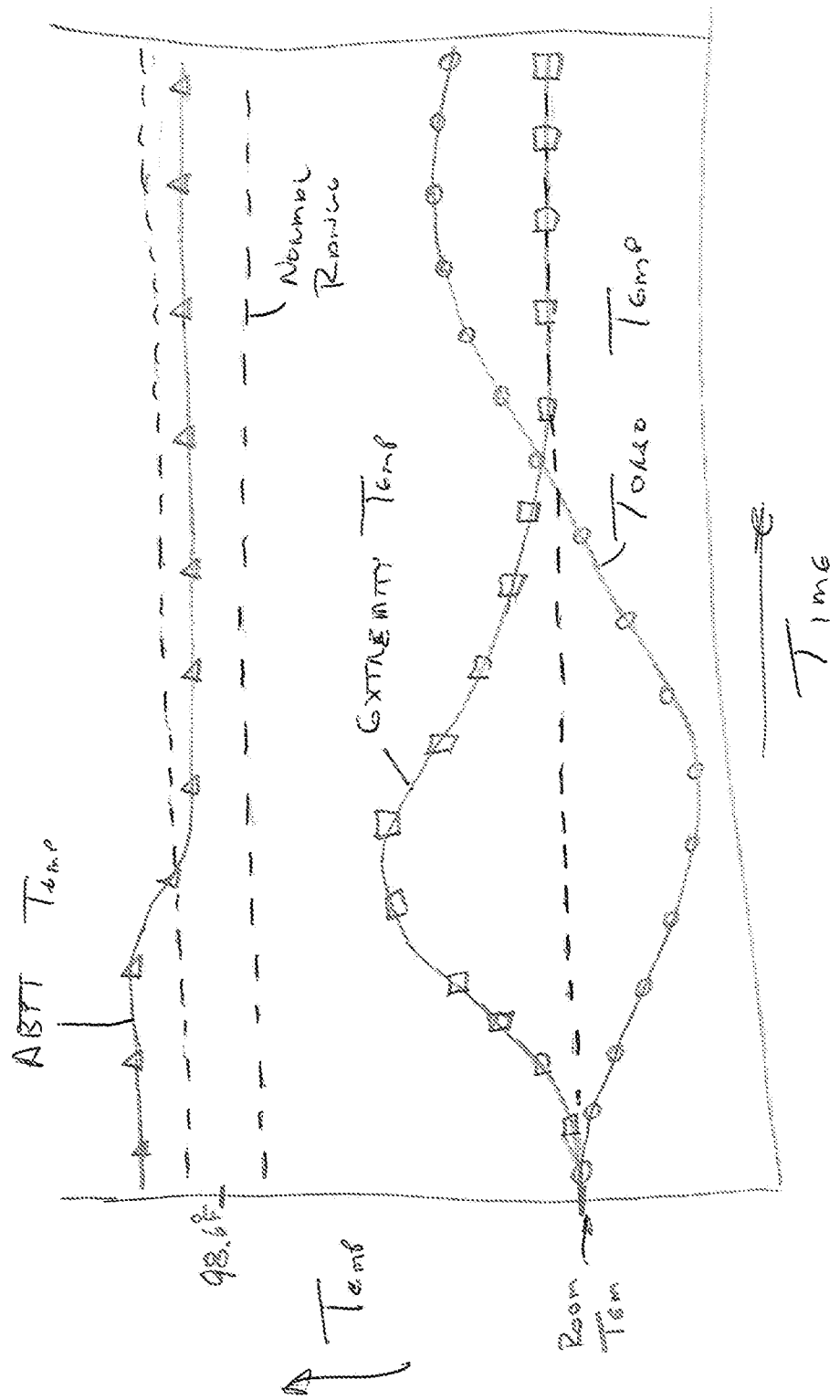
FIG. 13 shows an exemplary graph of representative temperatures for treatment of a hyperthermic patient or subject.

FIG. 13 shows an exemplary graph of representative temperatures for treatment of a hyperthermic patient or subject. An exemplary system determines core temperature via ABTT terminus 10. Once the hyperthermic condition is determined, an exemplary system begins heating/cooling the extremities and torso, though opposite to each other (extremities heated, torso cooled) to cause the brain to move cooler torso blood to cool internal organs and brain core. The torso temperature is slowly and steadily decreased to a predetermined maximum temperature while the extremities are warmed to a predetermined minimum temperature. Warming and cooling at a maximum predetermined rate, such as 0.5 degrees Fahrenheit per minute, reduces the risk of shock. As the ABTT temperature decreases into the normal range, extremity warming is slowly reduced while torso cooling is similarly slowly reduced until normal temperatures are obtained and are stable.

While various embodiments of the disclosure have been shown and described, it is understood that these embodiments are not limited thereto. The embodiments can be changed, modified, and further applied by those skilled in the art. Therefore, these embodiments are not limited to the detail shown and described previously, but also include all such changes and modifications.

I claim:

1. A brain temperature modification system, comprising:
a horizontally-extending patient support device for supporting a patient;
a plurality of temperature modification devices positioned on the support device, including at least one temperature modification device positioned to provide heat to or to remove heat from a respective one of a plurality of extremities of the patient, each of the plurality of temperature modification devices formed of a flexible material;
at least one temperature sensor sized and dimensioned to acquire a temperature measurement from an Abreu brain thermal tunnel (ABTT) terminus located between an eye and an eyebrow of the patient and configured to transmit a signal representative of the temperature measurement; and
a controller that includes a power supply, a processor, a non-transitory memory, an input module, and a display, wherein the processor is configured to receive the signal from the at least one temperature sensor, the processor is configured to determine from the signal a hypothermic condition or a hyperthermic condition of the patient, to control the plurality of temperature modification devices to remove heat from at least one of the plurality of extremities when the hypothermic condition is determined, and to control the plurality of temperature modification devices to provide heat to at least one of the plurality of extremities when the hyperthermic condition is detected.

2. The brain temperature modification system of claim 1, further comprising
a headgear comprising:
a support portion; and
at least one adjustable arm supported on the support portion.

3. The brain temperature modification system of claim 2, wherein the at least one temperature sensor is positioned on an end of the adjustable arm.

4. The brain temperature modification system of claim 2, wherein at least one of the plurality of temperature modification devices is arranged on the at least one adjustable arm.

5. The brain temperature modification system of claim 1, wherein the at least one temperature modification device is provided adjacent to the at least one temperature sensor.

6. The brain temperature modification system of claim 1, further comprising
a hand interface comprising:
an interior portion configured to allow a hand of the patient to be placed inside the hand interface; and
an exterior portion comprising an outer surface of the hand interface,
wherein the at least one temperature modification device is provided on the exterior portion.

7. The brain temperature modification system of claim 6, wherein
the hand interface further comprises a hand temperature sensor that is arranged at the interior portion and is configured to measure the temperature of the skin of the hand.

8. The brain temperature modification system of claim 6, wherein
the hand interface is electrically connected to the processor via a wire.

9. The brain temperature modification system of claim 1, further comprising
a foot interface comprising:
an interior portion configured to allow a foot of the patient to be placed inside the foot interface; and
an exterior portion comprising the outer surface of the foot interface,
wherein the at least one temperature modification device is provided on the exterior portion.

10. The brain temperature modification system of claim 9, wherein
the foot interface further comprises a foot temperature sensor that is arranged at the interior portion and is configured to measure the temperature of the skin of the foot.

11. The brain temperature modification system of claim 9, wherein
the foot interface is electrically connected to the processor via a wire.

12. The brain temperature modification system of claim 1, further comprising
a torso interface, comprising:
an upper portion configured to cover a torso of the patient; and
a lower portion configured for being arranged under the torso of the patient,
wherein the at least one temperature modification device is arranged on the torso interface, and
the upper portion and the lower portion are arranged to surround the torso of the patient such that a front and back of the torso of the patient can be warmed or cooled with the at least one temperature modification device.

13. A brain temperature modification system, comprising:
a horizontally-extending patient support device for supporting a patient;
a headgear supported on the patient support device, comprising a support portion, and at least one adjustable arm supported on the support portion, the at least one adjustable arm having, at an end thereof, at least one temperature sensor sized and dimensioned to acquire a temperature measurement from an Abreu brain thermal tunnel (ABTT) terminus located between an eye and an eyebrow of the patient and configured to transmit a signal representative of the temperature measurement;
a hand interface supported on the patient support device, comprising an interior portion configured to allow a hand of the patient to be placed inside the hand interface, an exterior portion comprising an outer surface of the hand interface, and at least one hand temperature modification device provided on the exterior portion to provide heat to or to remove heat from the hand;
a foot interface supported on the patient support device, comprising an interior portion configured to allow a foot of the patient to be placed inside the foot interface, an exterior portion comprising an outer surface of the foot interface, and at least one foot temperature modification device provided on the exterior portion to provide heat to or to remove heat from the foot; and
a processor configured to receive the signal from the at least one temperature sensor, the processor configured to determine from the signal a hypothermic condition or a hyperthermic condition of the patient, to control the hand temperature modification device and the foot temperature modification device to remove heat from the hand or the foot when the hypothermic condition is determined, and to control the hand temperature modification device and the foot temperature modification device to provide heat to the hand or the foot when the hyperthermic condition is detected.

14. The brain temperature modification system of claim 13, wherein
the hand interface further comprises a hand temperature sensor that is arranged at the interior surface and is configured to measure the temperature of the skin of the hand.

15. The brain temperature modification system of claim 13, wherein
the foot interface further comprises a foot temperature sensor that is arranged at the interior surface and is configured to measure the temperature of the skin of the foot.

16. The brain temperature modification system of claim 13, wherein
the processor, the headgear, the hand interface and the foot interface are electrically connected to each other by at least one wire to allow for the transfer of signals from the headgear, the hand interface and the foot interface to and from the processor.

17. The brain temperature modification system of claim 13, further comprising
a torso interface, comprising:
a torso temperature modification device;
an upper portion configured to cover a torso of the patient; and
a lower portion configured for being arranged under the patient,
wherein the upper portion and the lower portion are arranged to surround the torso of the patient such that a front and back of the patient can warm or cool the torso of the patient with the torso temperature modification device.

18. The brain temperature modification system of claim 17, wherein
the processor and the torso interface are electrically connected to each other by at least one wire to allow for the transfer of signals from the torso interface to and from the processor.

19. The brain temperature modification system of claim 13, further comprising:
a controller that includes a power supply, the processor, a non-transitory memory, an input module, and a display.

* * * * *